United States Patent
Millet

(10) Patent No.: US 11,185,518 B2
(45) Date of Patent: *Nov. 30, 2021

(54) S-BETA-HYDROXYBUTYRATE COMPOUNDS AND COMPOSITIONS ENRICHED WITH S-ENANTIOMER

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,886

(22) Filed: Feb. 6, 2020

(65) Prior Publication Data

US 2020/0170982 A1 Jun. 4, 2020

Related U.S. Application Data

(60) Continuation-in-part of application No. 16/272,192, filed on Feb. 11, 2019, now Pat. No. 10,596,130, which is a continuation-in-part of application No. 16/224,485, filed on Dec. 18, 2018, now Pat. No. 10,596,128, which is a division of application No. 15/936,849, filed on Mar. 27, 2018, now Pat. No. 10,245,243.

(60) Provisional application No. 62/607,578, filed on Dec. 19, 2017.

(51) Int. Cl.

| | |
|---|---|
| *A61K 31/19* | (2006.01) |
| *A61K 47/14* | (2017.01) |
| *A61K 9/14* | (2006.01) |
| *A61K 9/20* | (2006.01) |
| *A61K 9/48* | (2006.01) |
| *A61P 3/08* | (2006.01) |
| *A23L 29/00* | (2016.01) |
| *A23L 33/12* | (2016.01) |
| *A23L 33/00* | (2016.01) |
| *A23L 33/10* | (2016.01) |
| *A23L 33/155* | (2016.01) |

(52) U.S. Cl.
CPC ........... *A61K 31/19* (2013.01); *A23L 29/035* (2016.08); *A23L 33/10* (2016.08); *A23L 33/12* (2016.08); *A23L 33/30* (2016.08); *A61K 9/14* (2013.01); *A61K 9/20* (2013.01); *A61K 9/48* (2013.01); *A61K 47/14* (2013.01); *A61P 3/08* (2018.01); *A23L 33/155* (2016.08); *A23V 2002/00* (2013.01); *A23V 2250/182* (2013.01); *A23V 2250/192* (2013.01); *A23V 2250/1946* (2013.01); *A23V 2250/7106* (2013.01)

(58) Field of Classification Search
CPC ..... A61K 31/19; A61K 9/0053; A61K 31/047
See application file for complete search history.

(56) References Cited

U.S. PATENT DOCUMENTS

| | | | |
|---|---|---|---|
| 2,238,149 | A | 4/1941 | Aeckerle |
| 2,976,073 | A | 3/1961 | Russell et al. |
| 4,627,808 | A | 12/1986 | Hughes |
| 4,997,976 | A | 3/1991 | Brunengraber et al. |
| 5,093,044 | A | 3/1992 | Wretlind |
| 5,116,868 | A | 5/1992 | Chen et al. |
| 5,288,512 | A | 2/1994 | Seiden |
| 5,292,774 | A | 3/1994 | Hiraide et al. |
| 5,654,266 | A | 8/1997 | Chen et al. |
| 5,700,670 | A | 12/1997 | Yamagishi et al. |
| 6,207,856 | B1 | 3/2001 | Veech |
| 6,316,038 | B1 | 11/2001 | Veech |
| 6,323,237 | B1 | 11/2001 | Veech |
| 6,380,244 | B2 | 4/2002 | Martin et al. |

(Continued)

FOREIGN PATENT DOCUMENTS

| | | |
|---|---|---|
| CN | 1347319 | 5/2002 |
| EP | 2283834 | 2/2011 |

(Continued)

OTHER PUBLICATIONS

Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
First Examination Report for New Zealand Patent Application No. 711433 issued by the New Zealand Intellectual Property Office dated Mar. 10, 2016.
First Office Action issued by the Chinese State Intellectual Property Office dated Nov. 4, 2016 for corresponding Chinese Patent Application No. 201480016818.0.
Karppanen et al., J. Human Hypertension (2005), vol. 19, pp. S10-S19. (Year: 2005).

(Continued)

*Primary Examiner* — Dennis Heyer
(74) *Attorney, Agent, or Firm* — Workman Nydegger

(57) ABSTRACT

Ketogenic compositions include a mixture of optically pure S-beta-hydroxybutyrate salts and acid(s) or non-racemic mixture of beta-hydroxybutyrate salts and acid(s) enriched with the S-enantiomer. The S-beta-hydroxybutyrate enantiomer modulates the effect of ketone bodies in the subject and controls the rate at which ketosis is achieved. Beta-hydroxybutyric acid is more rapidly absorbed and utilized by the body than salts or esters, enhances taste, and reduces the need to include citric acid or other edible acids. Beta-hydroxybutyrate salts are more slowly absorbed and utilized by the body and can provide one or more electrolytes. Compositions for controlling ketone body level in a subject may contain a dietetically or pharmaceutically acceptable carrier and optically pure S-beta-hydroxybutyrate or non-racemic mixture enriched with S-beta-hydroxybutyrate, wherein the compositions contains from about 50.5% to 100% by enantiomeric equivalents of S-beta-hydroxybutyrate and from about 49.5% to 0% by enantiomeric equivalents of R-beta-hydroxybutyrate.

24 Claims, No Drawings

(56) References Cited

U.S. PATENT DOCUMENTS

| | | |
|---|---|---|
| 6,613,356 B1 | 9/2003 | Vlahakos |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2* | 9/2015 | D'Agostino ......... A61K 31/047 |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |
| 10,292,592 B2 | 5/2019 | Marshall et al. |
| 10,588,877 B2 | 3/2020 | Arnold |
| 10,660,958 B2 | 5/2020 | Clarke |
| 10,736,861 B2 | 8/2020 | Millet |
| 2001/0014696 A1 | 8/2001 | Veech |
| 2001/0041736 A1 | 11/2001 | Veech |
| 2003/0022937 A1 | 1/2003 | Veech |
| 2005/0129783 A1 | 6/2005 | McCleary |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0253781 A1 | 10/2009 | Veech |
| 2010/0041751 A1 | 2/2010 | Henderson |
| 2010/0197758 A1 | 8/2010 | Andrews et al. |
| 2010/0298294 A1 | 11/2010 | Clarke |
| 2012/0071548 A1 | 3/2012 | Veech |
| 2012/0202891 A1 | 8/2012 | Stinchcomb et al. |
| 2013/0079406 A1 | 3/2013 | Veech |
| 2013/0337116 A1 | 12/2013 | Petralia |
| 2015/0065571 A1 | 3/2015 | Clarke et al. |
| 2015/0132280 A1 | 5/2015 | Lopez et al. |
| 2016/0193173 A1 | 7/2016 | Clarke et al. |
| 2016/0256411 A1 | 9/2016 | Aung-Din |
| 2017/0020844 A1 | 1/2017 | Galinski |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1* | 10/2017 | Cavaleri ................ A61K 36/82 |
| 2017/0296501 A1 | 10/2017 | Lowery et al. |
| 2017/0298339 A1 | 10/2017 | Hanson et al. |
| 2017/0304564 A1 | 10/2017 | DeHaan |
| 2018/0021274 A1* | 1/2018 | Arnold ..................... A61K 9/08 514/557 |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2019/0099394 A1 | 4/2019 | D'Agostino et al. |
| 2019/0167613 A1 | 6/2019 | Millet |
| 2019/0313682 A1 | 10/2019 | Nagel |

FOREIGN PATENT DOCUMENTS

| | | |
|---|---|---|
| EP | 3094321 | 5/2019 |
| EP | 2976073 | 8/2019 |
| JP | 11060434 | 3/1999 |
| JP | 2002521330 | 7/2002 |
| RU | 2345546 | 4/2008 |
| WO | WO8703808 | 7/1987 |
| WO | WO 98/41200 | 9/1998 |
| WO | WO 03/070823 | 8/2003 |
| WO | WO2005107724 | 11/2005 |
| WO | WO2007115282 | 10/2007 |
| WO | WO2008005818 | 1/2008 |
| WO | WO 2008/021394 | 2/2008 |
| WO | WO 2008/024408 | 2/2008 |
| WO | WO2011101171 | 8/2011 |
| WO | 2013/150153 A1 | 10/2013 |
| WO | WO 2014153416 | 9/2014 |
| WO | 2015/071811 A1 | 5/2015 |
| WO | 2015/156865 A1 | 10/2015 |
| WO | WO2016123229 | 8/2016 |
| WO | WO 2017/208217 | 12/2017 |
| WO | WO 2018/089863 | 5/2018 |
| WO | WO2019018683 | 1/2019 |
| WO | 2019/237152 A1 | 12/2019 |

OTHER PUBLICATIONS

Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.

Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.

Veech, et al., "Ketone Bodies Mimic the Life Span Extending Properties of Caloric Restriction", IUBMB Life Feb. 8, 2017.

Murray, Andrew J., et al. "Novel ketone diet enhances physical and cognitive performance", The FASEB Journal, Vo. Dec. 30, 2016.

Hashim, Sami A., et al., "Ketone body therapy: from the ketogenic diet to the oral administration of ketone ester", Journal of Lipid Research, vol. 55, 2014.

Nova Max Plus Glucose and Ketone Testing with One Monitor. Downloaded Apr. 1, 2015. http://www.novacares.com/nova-max-plus/.

Serum Ketones Test. MedlinePlus Medical Encyclopedia. Downloaded Apr. 1, 2015. http://www.nlm.nih.gov/medlineplus/ency/article/003498.htm.

It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.

A New Toy Measuring Blood Ketones. Diet Doctor, Aug. 21, 2012. Dowloaded Apr. 1, 2015. http://www.dietdoctor.com/a-new-toy-measuring-blood-ketoones.

Precision Xtra vs. NovaMax Plus: Ketone Meter Evaluation. Jimmy Moore's Livin' La Vida Low Carb Blog. Downloaded Apr. 1, 2015. http://livinlavidalowcarb.com/blog/precision-xtra-vs-novamax-plus-ketone-meter-evaluation/15918.

Kirsch, JR et al. "Butanediol Induced Ketosis Increases Tolerance to Hypoxia in the Mouse." Stroke. 1980. vol. 11, No. 5, pp. 506-513.

Kossoff, Eric H. et al. "Optimal Clinical Management of Children Receiving the Ketogenic Diet Recommendations of the International Ketogenic Diet Study Group." Epilepsia, Feb. 2009;50(2):304-17. Epub Sep. 23, 2008.

Henderson, Samuel T. "Ketone Bodies as a Therapeutic for Alzheimer's Disease." Neurotherapeutics. Jul. 2008;5 3 3):470-80.

Krotkiewski, M. "Value of VLCD Supplementation with Medium Chain Triglycerides." I'nt J Obes Relat Metab Disord. Sep. 2001;25(9):1 393/\00.

PCT International Search Report and Written Opinion issued by the International Searching Authority dated Jul. 15, 2014 or International Patent Application No. PCT/US2014/031237.

Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).

Parker, Steve, "Ketogenic Mediterranean Diet: Version 2.3," Nov. 23, 2010, pp. 1-3. (Year: 2010).

Sajewicz et al. in Journal of Liquid Chromatography & Related Technologies, 33:1047-1057 (2010) (Year: 2010).

Shigeno etal. in Biosci. Biotech. Biochem., 56(2), 320-323 (1992) (Year: 1992).

Optical Purity and Enantiomeric Excess at https://www.masterorganicchemistry.com/2017/02/24/optical-purity-and-enantiomeric-excess/. (Retrieved from the internet Nov. 6, 2018) (Year: 2018).

(56) References Cited

OTHER PUBLICATIONS

Tisdale, "Reduction of weight loss and tumour size in a cachexia model by a high fat diet", British Journal of Cancer, Jul. 1987, vol. 56, p. 39-43.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
International Search Report cited in PCT/US19/27214 dated Jun. 25, 2019.
Written Opinion cited in PCT/US19/27214 dated Jun. 25, 2019.
International Search Report cited in PCT/US18/62093 dated Feb. 1, 2019.
International Search Report cited in PCT/US18/62096 dated Feb. 11, 2019.
Pubchem, "Acetoacetic acid" Electronic Resource https://pubchem.ncbi.nim.nih.gov/compound/Acetoacetic-acid, Retrieved on Sep. 3, 2019.
Arendash et al. "Caffeine and Coffee as Therapeutics Against Alzheimer's Disease", Journal of Alzheimer's Disease 20, 2010, S117-S126.
Kesl, et al., "Effects of exogenous ketone supplementation on blood ketone, glucose, triglyceride, and lipoprotein levels in Sprague-Dawley rats", Nutrition & Metabolism (2016).
Extended European Search Report issued in PCT/US2017021886 dated Oct. 17, 2019.
International Search Report and Written Opinion issued in PCT/US19/48364 dated Nov. 15, 2019.
International Search Report and Written Opinion issued in PCT/US19/48357 dated Nov. 18, 2019.
Karppanen, H., et al., "Why and how to implement sodium, potassium, calcium, and magnesium changes in food items and diets?"
U.S. Appl. No. 14/455,385, filed Jan. 2, 2015, Office Action.
U.S. Appl. No. 14/860,092, filed Mar. 9, 2016, Office Action.
U.S. Appl. No. 14/860,092, filed Oct. 17, 2016, Office Action.
U.S. Appl. No. 15/610,668, filed Jul. 25, 2018, Office Action.
U.S. Appl. No. 15/454,157, filed Jan. 11, 2018, Office Action.
U.S. Appl. No. 15/454,157, filed Jun. 13, 2018, Office Action.
U.S. Appl. No. 15/936,820, filed Nov. 14, 2018, Office Action.
U.S. Appl. No. 15/936,849, filed Nov. 14, 2018, Office Action.
U.S. Appl. No. 15/454,157, filed Feb. 26, 2019, Notice of Allowance.
U.S. Appl. No. 15/936,849, filed Jan. 24, 2019, Notice of Allowance.
U.S. Appl. No. 16/272,328, filed Jul. 29, 2019, Office Action.
U.S. Appl. No. 16/272,359, filed Feb. 11, 2019, Notice of Allowance.
U.S. Appl. No. 16/381,202, filed Oct. 22, 2019, Office Action.
U.S. Appl. No. 16/224,485, filed Nov. 27, 2019, Notice of Allowance.
U.S. Appl. No. 16/224,408, filed Nov. 27, 2019, Notice of Allowance.
U.S. Appl. No. 16/272,145, filed Jan. 10, 2020, Office Action.
U.S. Appl. No. 16/409,501, filed Jan. 14, 2020, Notice of Allowance.
International Search Report and Written Opinion received for PCT Patent Application No. PCT/US2020/033159, dated Aug. 12, 2020, 9 pages.
International Search Report and Written Opinion issued in PCT/US20/16952 dated Apr. 22, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion issued in PCT/US20/17552 dated May 4, 2020.
A New Toy Measuring Blood Ketones Diet Doctor, Aug. 21, 2012. Downloaded Apr. 1, 2015. http://www.dietdoctor.com/a-new-toy-measuring-blood-ketoones.
Bastin et al., "Salt Slection and Optimisation Procedures for Pharmaceutical New Chemical Entities", American Chemical Society and The Royal Society of Chemistry, vol. 4, No. 5, 2000, pp. 427-435.
Dolson, Laura. How to Test Your Blood for Ketones. Downloaded Apr. 1, 2015. http://lowcarbdiets.about.eom/od/KetogenicDiets/a/How-to-Test-Blood-For Ketones.htm.
Haywood A, Glass BD. Pharmaceutical excipients—where do we begin? Australian Prescriber. 2011; 34:112-114.
International Preliminary Report on Patentability received for PCT Patent Application No. PCT/US2019/048364, dated Mar. 11, 2021, 7 pages.
International Search Report and Written Opinion received for PCT Patent Application No. PCT/US21/17078, dated Apr. 23, 2021, 9 pages.
Robson et al. Expert Opin. Drug Saf. (2011), vol. 10, pp. 675-685 (Year: 2011).
Amazon, "Perfect Keto Perform Pre Workout Powder—Bum Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Holtzman et al., "Role of adenosine receptors in caffeine tolerance", J. Pharmacol. Exp. Ther., 1991 ;256(1 ):62-68.
International Search Report and Written Opinion received for PCT Patent Application No. PCT/US20/37289, dated Sep. 30, 2020, 8 pages.
Non-Final Office Action received for U.S. Appl. No. 16/381,202, dated Aug. 11, 2020, 8 pages.
Non-Final Office Action received for U.S. Appl. No. 16/720,211, dated Oct. 28, 2020, 14 pages.
Non-Final Rejection dated Sep. 9, 2020 for U.S. Appl. No. 16/783,956.
Notice of Allowance received for U.S. Appl. No. 16/381,202, dated Nov. 10, 2020, 8 pages.
Office Action cited in U.S. Appl. No. 16/720,211 dated Oct. 28, 2020.
Parker, Steve, "Ketogenic Mediterraanean Diet: Version 2.3," Nov. 23, 2010, pp. 1-3. (Year: 2010).
Requirement for Restriction/Election received for U.S. Appl. No. 16/551,570, dated Sep. 28, 2020, 6 pages.
Vandenberghe et al. in Can. J. Physiol. Pharmacol. 95:455-458 (2017) (Published at www.nrcresearchpress.com/cjpp on Nov. 25, 2016). (Year: 2016).
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
Malo, M. S. et al. Intestinal alkaline phosphatase preserves the normal homeostasis of gut microbiota, 2010, Gut, 59, 1476-1484 (Year: 2010).

* cited by examiner

S-BETA-HYDROXYBUTYRATE COMPOUNDS AND COMPOSITIONS ENRICHED WITH S-ENANTIOMER

CROSS-REFERENCE TO RELATED APPLICATIONS

This Application is a continuation-in-part of U.S. patent application Ser. No. 16/272,192, filed Feb. 11, 2019, now U.S. Pat. No. 10,596,130, which is a continuation-in-part of U.S. patent application Ser. No. 16/224,485, filed Dec. 18, 2018, now U.S. Pat. No. 10,596,128, which is a division of U.S. patent application Ser. No. 15/936,849, filed Mar. 27, 2018, now U.S. Pat. No. 10,245,243, which claims the benefit of U.S. Provisional Patent Application No. 62/607,578, filed Dec. 19, 2017, the disclosures of which are incorporated herein by reference in their entirety.

BACKGROUND

1. Field of the Invention

Disclosed herein are S-beta-hydroxybutyrate compounds, non-racemic beta-hydroxybutyrate compounds, salts, acids, and esters thereof, and compositions enriched with the S-enantiomer of beta-hydroxybutyrate and methods for controlling and/or modulating blood levels and/or the effects of ketone bodies in a subject.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation and use of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. At blood levels between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

During ketosis, the body is in ketogenesis and essentially burning fat for its primary fuel. The body cleaves fats into fatty acids and glycerol and transforms fatty acids into acetyl CoA molecules, which are then eventually transformed through ketogenesis into the water-soluble ketone bodies beta-hydroxybutyrate (i.e., "β-hydroxybutyrate" or "BHB"), acetoacetate (also known as acetylacetonate), and acetone in the liver. Beta-hydroxybutyrate and acetoacetate are the primary ketone bodies used by the body for energy while acetone is removed and expelled as a by-product of ketogenesis.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is by fasting combined with exercise. This is physically and emotionally demanding and is extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as the "low-carb flu." In addition, many people experience a down regulation in their metabolism as the body naturally goes into an "energy-saving" mode. Some suggest that these transitory symptoms may last as long as two to three weeks. During this transition period, if a subject consumes a meal or snack containing carbohydrates above the restrictive amount, there is an immediate termination of ketogenisis, exiting the body from its state of ketosis, as the body shifts back to glucose utilization for its primary fuel and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis effects the rate at which certain electrolytes are extracted by the kidneys, additionally lowering electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

Some compositions used to promote ketosis in a mammal include a racemic mixture of beta-hydroxybutyrate (RS-beta-hydroxybutyrate or DL-beta-hydroxybutyrate). Other compositions, such as those disclosed in U.S. Patent Publication No. 2017/0296501 to Lowery et al., contain the endogenous form of beta-hydroxybutyrate, or R-beta-hydroxybutyrate, while Lowery et al. discourage use of the non-endogenous enantiomer, or S-beta-hydroxybutyrate. Others, such as those disclosed in U.S. Pat. No. 8,642,654 to Clarke et al., consist mostly or entirely of a single beta-hydroxybutyrate ester (3R)-hydroxybutyl (3R)-hydroxybutyrate. Other enantiomers, such as (3R)-hydroxybutyl (3 S)-hydroxybutyrate, (3 S)-hydroxybutyl (3R)-hydroxybutyrate, and (3 S)-hydroxybutyl (3 S)-hydroxybutyrate, are mostly or entirely omitted. The omission of enantiomers that are not the endogenous form of beta-hydroxybutyrate is based on the view that S-beta-hydroxybutyrate (aka (3S)-hydroxybutyrate) is ineffective or even harmful.

BRIEF SUMMARY

Disclosed herein are compositions and methods for controlling ketone body levels in a subject, including promoting and/or sustaining ketosis in a subject over an extended period of time. Example compositions include S-beta-hydroxybutyrate compounds and non-racemic mixtures of S-beta-hydroxybutyrate and R-beta-hydroxybutyrate, wherein the non-racemic mixtures are enriched with the S-beta-hydroxybutyrate enantiomer relative to the R-beta-hydroxybutyrate enantiomer, such as by including 51% to 99.5% by enantiomeric equivalents of the S-beta-hydroxybutyrate enantiomer and 49.5% to 0.5% by enantiomeric equivalents of the R-beta-hydroxybutyrate enantiomer.

Non-racemic mixtures of S-beta-hydroxybutyrate and R-beta-hydroxybutyrate contain more of the S-beta-hydroxybutyrate enantiomer than the endogenous form (R-enantiomer) produced by a mammal in order to provide a more controlled and sustained ketogenic effect compared to a racemic mixture and/or compositions enriched with the R-enantiomer. Because the R-beta-hydroxybutyrate enantiomer is endogenously produced by a mammal during ketosis, administering the R-beta-hydroxybutyrate enantiomer to a subject provides a quantity that can be immediately utilized by the body, such as for producing energy (e.g., as an alternative energy source to glucose). However, this effect is modulated and extended when the S-enantiomer is the predominant component.

Contrary to compositions that are deliberately enriched with the R-enantiomer or that minimize or eliminate S-beta-hydroxybutyrate altogether, the non-racemic mixture is enriched with the S-beta-hydroxybutyrate enantiomer, which is not endogenously produced by a mammal, in order to produce one or more desired effects in the mammal, as discussed herein.

In addition, while conventional compositions typically contain polymer, oligomer, ester, or salt forms of beta-hydroxybutyrate, the S-beta-hydroxybutyrate compounds and non-racemic mixtures enriched with S-beta-hydroxybutyrate relative to R-beta-hydroxybutyrate can include the free acid form of S-beta-hydroxybutyrate and/or R-beta-hydroxybutyrate. For example, the S-beta-hydroxybutyrate compound or non-racemic mixture may contain one or more salts or esters of optically pure S-beta-hydroxybutyrate, or a non-racemic mixture of S-beta-hydroxybutyrate and R-beta-hydroxybutyrate, in combination with S-beta-hydroxybutyric acid, and optionally R-beta-hydroxybutyric acid. Combining beta-hydroxybutyric acid with one or more beta-hydroxybutyrate salts is beneficial because it reduces electrolyte load, increases absorption rate, improves taste, facilitates easier formulation, and reduces the need to add citric acid or other edible acids to obtain a composition having neutral or acidic pH.

In some embodiments, the compositions disclosed herein can be used in a method for increasing ketone body level in a subject, including promoting and/or sustaining ketosis in a subject, comprising administering to a subject in need thereof a nutritionally or pharmaceutically effective amount of one or more compositions disclosed herein. Examples of beneficial effects of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, administering the S-beta-hydroxybutyrate or non-racemic mixture of S-beta-hydroxybutyrate and R-beta-hydroxybutyrate in the enantiomeric ratios or percentages disclosed herein provide one or more of: increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

In some embodiments, the composition may include a nutritionally or pharmaceutically acceptable carrier.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Definitions

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

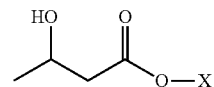

where,

X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

In some cases, the composition can include a mixture of one or more beta-hydroxybutyrate salts and beta-hydroxybutyric acid(s). Providing S-beta-hydroxybutyrate in its acid form can be beneficial because of its much quicker absorption response time compared to the salt form. Nonetheless, even though the acid form by itself is a liquid with extremely low pH and unpalatable taste, when made or combined with the salt form(s) and where the amount of beta-hydroxybutyric acid is small relative to the salt form(s), the composition can still form a solid, powder or other form typical of the salt form(s). In such case, the combined salt and acid form of BHB has acceptable pH and taste. BHB compositions that include both salt and acid forms have advantages, such as increased absorption rate, increased bioavailability, lower electrolyte load, ease of manufacture, significantly improved taste, and reduced need for citric acid or other edible acids to obtain a composition with neutral or acidic pH. It will be appreciated that beneficial effects can also be provided using a mixture of BHB salt(s) and/or ester(s) and the acid form(s) of BHB.

The term "free beta-hydroxybutyric acid" means the sum of non-deprotonated and deprotonated beta-hydroxybutyric acid molecules. A deprotonated beta-hydroxybutyric acid molecule generally means a molecule that has released a proton to form a hydronium ion ($H_3O+$) and a beta-hydroxybutyrate anion (e.g., dissolved in water).

Free beta-hydroxybutyric acid molecules are typically not deprotonated to any significant degree when contained in a beta-hydroxybutyrate mixed salt-acid composition in dry powder or other solid form. In such cases, the fractional amount of free beta-hydroxybutyric acid in a beta-hydroxybutyrate mixed salt-acid composition on a weight basis is the weight of free beta-hydroxybutyric acid divided by the combined weight of free beta-hydroxybutyric acid and beta-hydroxybutyrate salt(s). On a molar basis, the fractional amount of free beta-hydroxybutyric acid in an beta-hydroxybutyrate mixed salt-acid composition are the molar equivalents of free beta-hydroxybutyric acid divided by the sum of molar equivalents of free beta-hydroxybutyric acid and beta-hydroxybutyrate anions provided by the beta-hydroxybutyrate salt(s).

When dissolved in water, a portion of the beta-hydroxybutyric acid will typically dissociate into beta-hydroxybutyrate anions and hydronium ions ($H_3O+$). As a result, beta-hydroxybutyric acid molecules can exchange protons and cations with dissolved beta-hydroxybutyrate salts. For purposes of defining the relative amounts of beta-hydroxybutyric acid and beta-hydroxybutyrate salt(s) in a beta-hydroxybutyrate mixed salt-acid composition, dissociation of beta-hydroxybutyric acid molecules and the exchange of protons and cations is not understood as changing the molar ratio of free beta-hydroxybutyric acid relative to beta-hydroxybutyrate anions from the beta-hydroxybutyrate salt(s). The total quantity of free beta-hydroxybutyric acid molecules in solution is the sum of dissolved beta-hydroxybutyric acid molecules that are not deprotonated and beta-hydroxybutyrate anions formed by deprotonation of beta-hydroxybutyric acid molecules.

Stated another way, the total molar equivalents of beta-hydroxybutyric acid in solution, whether or not deprotonated, is understood to be the difference between (i) the sum of molar equivalents of non-deprotonated beta-hydroxybutyric acid molecules and total molar equivalents of beta-hydroxybutyrate anions in solution (from all sources) and (ii) the total molar equivalents of cationic charge provided by cations from the beta-hydroxybutyrate salt compounds (which equals the total molar equivalents of beta-hydroxybutyrate anions provided by the beta-hydroxybutyrate salt(s)). Alkali metal cations such as sodium and potassium provide 1 mole of cationic charge per mole of metal cations. Alkaline earth metal cations such as magnesium and calcium, on the other hand, provide 2 moles of cationic charge per mole of metal cations. 1 mole of deprotonated beta-hydroxybutyric acid molecules provide 1 mole of anionic charge and one mole of cationic charge.

In view of the foregoing, the molar fraction of beta-hydroxybutyric acid in solution in relation to total moles of beta-hydroxybutyrate molecules from the beta-hydroxybutyrate mixed salt-acid composition in solution is $[(i)-(ii)\div(i)]$, and the molar fraction of beta-hydroxybutyrate molecules from the beta-hydroxybutyrate salt(s)) in solution is $[(ii)\div(i)]$. Multiplying the molar fraction of each by 100 gives the percentage of each in solution.

By way of example, if 100 molar equivalents of beta-hydroxybutyrate mixed salt-acid composition in a dry powdered state contained 5% of free non-deprotonated beta-hydroxybutyric acid and 95% beta-hydroxybutyrate salt(s) on a molar basis, there would be essentially 5 molar equivalents of beta-hydroxybutyric acid molecules and 95 molar equivalents of beta-hydroxybutyrate anions. When there is sufficient water to dissolve the beta-hydroxybutyrate salt(s), and if a portion of the beta-hydroxybutyric acid molecules were deprotonated, the molar equivalents of non-deprotonated beta-hydroxybutyric acid would be less than 5, and the molar equivalents of beta-hydroxybutyrate anions would be greater than 95. The extent of deprotonation of beta-hydroxybutyric acid in solution is related to solution pH.

Whether beta-hydroxybutyrate is the S- or R-enantiomer depends on the tetrahedral orientation of the hydroxy (or oxy group in the case of an ester) on the 3-carbon (beta-carbon) in relationship to the planar carboxyl group.

Beta-hydroxybutyrate, typically R-beta-hydroxybutyrate, which is the endogenous form, can be utilized by a patient's body as a fuel source during instances of low glucose levels in the subject or when a patient's body is supplemented with a usable form of beta-hydroxybutyrate. Beta-hydroxybutyrate is commonly referred to as a "ketone body".

As used herein, a "ketogenic composition" is formulated to increase ketone body level in a subject, including inducing and/or sustaining a state of elevated ketone bodies at a desired level, such as ketosis, in a subject to which it is administered.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

The term "short chain triglycerides" (SCT) refers to molecules having a glycerol backbone attached to three medium chain fatty acids. Short chain fatty acids can range from 2 to 5 carbon atoms in length. Exemplary short chain fatty acids are acetic acid, propionic acid, butyric acid, isobutyric acid, valeric acid, and isovaleric acid. An example SCT is tributyrin.

The term "medium chain triglycerides" (MCT) refers to molecules having a glycerol backbone attached to three medium chain fatty acids. Medium chain fatty acids can range from 6 to 12 carbon atoms in length, and more likely 8 to 10 carbon atoms in length. Exemplary fatty acids are caprylic acid, also known as octanoic acid, comprising 8 carbon molecules, and capric acid, also known as decanoic acid, comprising 10 carbon molecules. MCTs, medium chain fatty acids, and mono- and di-glycerides are ketone body precursors that can provide an additional source for the production of ketone bodies independent of beta-hydroxybutyrate.

The term "long chain triglycerides" (LCT) refers to molecules having a glycerol backbone attached to three medium chain fatty acids. Long chain fatty acids can be greater than 12 carbon atoms in length.

The term "administration" or "administering" is used herein to describe the process in which the disclosed compositions are delivered to a subject. The composition may be administered in various ways including oral, intragastric, and parenteral (referring to intravenous and intra-arterial and other appropriate parenteral routes), among others.

II S-beta-hydroxybutyrate Compounds And Non-Racemic Mixtures Enriched with S-beta-hydroxybutyrate Compositions for increasing ketone body level in a subject, including controlling and/or modulating ketosis, comprise optically pure (100%) S-beta-hydroxybutyrate or a non-racemic mixture of S-beta-hydroxybutyrate enriched with the S-enantiomer (i.e., more than 50% and less than 100% by enantiomeric equivalents of S-beta-hydroxybutyrate and less than 50% and more than 0% by enantiomeric equivalents of R-beta-hydroxybutyrate).

In some embodiments, non-racemic mixtures of S-beta-hydroxybutyrate and R-beta-hydroxybutyrate contain from 50.5% to 99.5%, 51% to 99%, 52% to 98%, 53% to 97%, 55% to 96%, 57% to 93%, 60% to 90%, or 65% to 85% by enantiomeric equivalents of the S-beta-hydroxybutyrate enantiomer and 49.5% to 0.5%, 49% to 1%, 48% to 2%, 47% to 3%, 45% to 4%, 3% to 7%, 40% to 10%, or 35% to 15% by enantiomeric equivalents of the R-beta-hydroxybutyrate enantiomer.

The non-racemic mixture of S-beta-hydroxybutyrate and R-beta-hydroxybutyrate contains more of the S-beta-hydroxybutyrate enantiomer rather than the endogenous form produced by a mammal, which is the R-beta-hydroxybutyrate enantiomer, in order to provide for more controlled, gradual, extended, and/or modulated ketogenic effect compared to either a racemic mixture or composition enriched with the R-beta-hydroxybutyrate enantiomer. Because the R-beta-hydroxybutyrate enantiomer is endogenously produced by a mammal during ketosis, administering the R-beta-hydroxybutyrate enantiomer to a subject provides an additional quantity and/or increased blood plasma level that can be immediately utilized by the body, such as for producing energy (e.g., as an alternative energy source to glucose). However, this effect is modulated and extended due to the S-enantiomer being the predominant component.

Contrary to compositions that deliberately minimize or eliminate S-beta-hydroxybutyrate, the non-racemic mixture contains a majority quantity of the S-beta-hydroxybutyrate enantiomer, which is not endogenously produced by a mammal, in order to produce one or more desired effects in the mammal. For example, administering S-beta-hydroxybutyrate along with R-beta-hydroxybutyrate can result in at least one of: (1) increased endogenous production of R-beta-hydroxybutyrate and acetoacetate; (2) endogenous conversion of the S-beta-hydroxybutyrate into one or both of R-beta-hydroxybutyrate and acetoacetate; (3) endogenous conversion of the S-beta-hydroxybutyrate into fatty acids and sterols; (4) prolonged ketosis; (5) metabolism of the S-beta-hydroxybutyrate independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate that modulates metabolism of R-beta-hydroxybutyrate and glucose; (10) antioxidant activity; and (11) production of acetyl-CoA.

The optically pure S-beta-hydroxybutyrate or non-racemic mixture of S-beta-hydroxybutyrate and R-beta-hydroxybutyrate can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, the composition may include a nutritionally or pharmaceutically acceptable carrier.

The S-beta-hydroxybutyrate and R-beta-hydroxybutyrate can be provided in various forms, such as salts and/or esters, together with a quantity of free acid form(s). The percent of enantiomer equivalents of each of the S-beta-hydroxybutyrate and R-beta-hydroxybutyrate is defined by the molar quantity of either S-beta-hydroxybutyrate or R-beta-hydroxybutyrate divided by the total molar quantities of S-beta-hydroxybutyrate and R-beta-hydroxybutyrate. The amounts of any cations forming salts and/or alcohols forming esters are excluded and do not count in determining the percent of enantiomeric equivalents of each of S-beta-hydroxybutyrate and R-beta-hydroxybutyrate. For example, the weight contributions of cations, alcohols, or complexing agents can be factored in so as to not tip the scale relative to enantiomeric equivalents of R-BHB and S-BHB.

In some embodiments, the optically pure S-beta-hydroxybutyrate or non-racemic mixture of S-beta-hydroxybutyrate and R-beta-hydroxybutyrate is provided in a composition that includes a dietetically or pharmaceutically acceptable carrier. Examples include powders, liquids, tablets, capsules, food products, food additives, beverages, vitamin fortified beverages, beverage additives, candies, suckers, pastilles, food supplements, sprays, injectables, and suppositories.

In some embodiments, the optically pure S-beta-hydroxybutyrate or non-racemic mixture of S-beta-hydroxybutyrate and R-beta-hydroxybutyrate can be provided as a salt, such as one or more salts of alkali metals, alkaline earth metals, transition metals, amino acids, or metabolites of amino acids. Examples include lithium salts, sodium salts, potassium salts, magnesium salts, calcium salts, zinc salts, iron salts (as iron II and/or iron III), chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts. In some embodiments, the salt is not a calcium salt of S-beta-hydroxybutyrate.

In some embodiments, the non-racemic mixture of S-beta-hydroxybutyrate and R-beta-hydroxybutyrate can be provided as one or more esters, such as mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono-ester of S-, R-, or S-R-1,3-butanediol, di-ester of S-, R-, or S-R-1,3-butanediol, mono-ester of glycerin, (3 S)-hydroxybutyl (3 S)-hydroxybutyrate mono-ester, (3R)-hydroxybutyl (3 S)-hydroxybutyrate, mono-ester, di-ester of glycerin, tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxy-carboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, and one or more polyacids, such as tartaric acid, citric acid, malic acid, succinic acid, and fumaric acid. While (3R)-hydroxybutyl (3R)-hydroxybutyrate mono-ester can be included, it should not cause the amount of R-hydroxybutyrate to exceed 48% by enantiomeric equivalents.

In some embodiments, optically pure S-beta-hydroxybutyrate can include one or more salt forms of S-beta-hydroxybutyrate in combination with a relatively minor amount of the acid form of S-beta-hydroxybutyrate. A non-racemic mixture can include one or more salt forms of S-beta-hydroxybutyrate and R-beta-hydroxybutyrate in combination with a relatively minor amount of the acid form(s) of S-beta-hydroxybutyrate and/or R-beta-hydroxybutyrate. The ratio of salt to acid forms of S-beta-hydroxybutyrate is not necessarily the same as the ratio of salt to acid forms of R-beta-hydroxybutyrate (when included). This allows for more flexibility and a broader range of advantages in controlling the pharmacokinetics and electrolyte balance of the composition.

In some embodiments, the optically pure S-beta-hydroxybutyrate or non-racemic mixture contains less than 100% of one or more beta-hydroxybutyrate salts and greater than 0% free beta-hydroxybutyric acid, such as up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, by molar equivalents of one or more S-beta-hydroxybutyrate and/or R-beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, by molar equivalents of free S-beta-hydroxybutyric acid and/or free R-beta-hydroxybutyric acid.

In the case where a non-racemic mixture contains a high amount of the S-enantiomer relative to the R-enantiomer, it is possible to use a higher ratio of free R-beta-hydroxybutyric acid relative to R-beta-hydroxybutyrate salt and still obtain a composition having neutral or other desired pH. That is, even if the relative amount of R-beta-hydroxybutyric acid is high relative to the R-beta-hydroxybutyrate salt, the overall amount of acid can be relatively small if the amount of S-beta-hydroxybutyrate salt is high.

In other embodiments, the non-racemic mixture can include one or more ester forms of optically pure S-beta-hydroxybutyrate, or a non-racemic mixture of S-beta-hydroxybutyrate and R-beta-hydroxybutyrate, in combination with a relatively minor amount of the acid form(s) of S-beta-hydroxybutyrate and/or R-beta-hydroxybutyrate. In yet other embodiments, the non-racemic mixture can include both salt and ester forms of S-beta-hydroxybutyrate and/or R-beta-hydroxybutyrate in combination with a relatively minor amount of the acid form(s) of S-beta-hydroxybutyrate and/or R-beta-hydroxybutyrate.

In some embodiments, the composition may include at least one medium chain fatty acid, or a mono-, di- or triglyceride of the at least one medium chain fatty acid, wherein the medium chain fatty acid has from 6 to 12 carbons, preferably from 8 to 10 carbons. The composition may include at least one short chain fatty acid, or a mono-, di- or triglyceride of the at least one short chain fatty acid, wherein the short chain fatty acid has less than 6 carbons. Though less preferred, the composition may include at least one long chain fatty acid, or a mono-, di- or triglyceride of the at least one long chain fatty acid, having more than 12 carbons.

Examples of short chain fatty acids include acetic acid, propionic acid, butyric acid, isobutyric acid, valeric acid, and isovaleric acid. Examples of medium chain fatty acids include caproic acid, caprylic acid, capric acid, and lauric acid. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

Examples and sources of the medium chain fatty acid, or an ester thereof such as a medium chain triglyceride, include coconut oil, coconut milk powder, fractionated coconut oil, palm oil, palm kernel oil, caprylic acid, capric acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

The administration of optically pure S-beta-hydroxybutyrate or a non-racemic mixture of S-beta-hydroxybutyrate and R-beta-hydroxybutyrate results in controlled, prolonged, and modulated blood levels of ketone bodies, thereby exploiting the metabolic and physiological advantages of sustained ketosis. Raising the levels of ketone bodies in the blood provides a subject with greater flexibility in diet options as compared to methods that aim to induce and sustain ketosis based on diet alone (e.g., based on fasting and/or limited carbohydrate intake). For example, a subject that has been administered an appropriate amount of a non-racemic mixture of S-beta-hydroxybutyrate and R-beta-hydroxybutyrate will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

In some embodiments, a ketogenic composition additionally includes a therapeutically effective amount of vitamin $D_3$. Vitamin $D_3$ is believed to work in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 µg to about 200 µg, or about 10 µg to about 100 µg, or about 15 µg to about 75 µg of vitamin $D_3$.

Some embodiments also include one or more additional ketone precursors or supplements. These additional ketone precursors or supplements might include acetoacetate, ketone esters, and/or other compounds that cause a rise in blood ketone levels without adding more electrolytes to the bloodstream. Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the otherwise poor taste of beta-hydroxybutyrate compounds. These include essential oils, such as peppermint, natural and artificial sweeteners, and other flavorants known in the art.

In some embodiments, ketogenic compositions may further include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), silica, phosphate salt (e.g., di- or tricalcium phosphate), talc, powdered cellulose, calcium carbonate, and the like.

III. Administration

In some embodiments, the compositions disclosed herein can be used in a method for increasing ketone body level, including promoting and/or sustaining ketosis, in a subject comprising administering to a subject in need thereof a nutritionally or pharmaceutically effective amount of one or more compositions disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

In some embodiments, administering the optically pure S-beta-hydroxybutyrate or non-racemic mixture of S-beta-hydroxybutyrate and R-beta-hydroxybutyrate in the enantiomeric ratios or percentages disclosed herein provide one or more of increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols;

prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

Ketogenic compositions described herein may be administered to a subject in therapeutically effective dosages and/or in frequencies to induce or sustain ketosis. In some embodiments, a single dose will include an amount of optically pure S-beta-hydroxybutyrate or non-racemic mixture of S-beta-hydroxybutyrate and R-beta-hydroxybutyrate ranging from about 0.5 gram to about 25 grams, or about 0.75 gram to about 20 grams, or about 1 gram to about 15 grams, or about 1.5 grams to about 12 grams.

In some embodiments, the ketogenic compositions can include or be administered together with other supplements, such as vitamin $D_3$, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

In some embodiments, the compositions may further include one or more medium chain fatty acids, fatty acid esters, or mono-, di- or triglycerides of medium chain fatty acids in order to provide an additional source of ketone bodies, as discussed herein, for sustaining ketosis for a longer period of time compared to the S-beta-hydroxybutyrate or non-racemic mixture of S-beta-hydroxybutyrate and R-beta-hydroxybutyrate by itself. In some embodiments, the composition is preferably administered such that the ratio of the S-beta-hydroxybutyrate or non-racemic mixture of S-beta-hydroxybutyrate and R-beta-hydroxybutyrate to medium chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, ketogenic compositions can be administered via oral administration in solid and/or powdered form, such as in a powdered mixture (e.g., powder filled gelatin capsules), hard-pressed tablets, or other oral administration route known to those skilled in the art.

In some embodiments, multiple doses of the composition are administered over a period of time. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

IV. Examples

The following is a description of exemplary S-beta-hydroxybutyrate and non-racemic mixtures of S-beta-hydroxybutyrate and R-beta-hydroxybutyrate compositions and other ketogenic compositions useful for raising ketone levels in a subject, including inducing and/or modulating a ketogenic state in a subject to which they are administered. It should be appreciated that the beta-hydroxybutyrate compounds described in the examples can be in the form of salts, esters, dimers, trimers, oligomers, and polymers, as discussed herein. The important thing from the standpoint of the examples is the enantiomeric percentages or ratios of S-beta-hydroxybutyrate and R-beta-hydroxybutyrate.

In some cases, the compositions can be a blend of beta-hydroxybutyrate salts, blend of beta-hydroxybutyrate esters, blend of beta-hydroxybutyrate salts and esters, blend of beta-hydroxybutyrate salts and free beta-hydroxybutyric acid(s), blend of beta-hydroxybutyrate esters and free beta-hydroxybutyric acid(s), or blend of beta-hydroxybutyrate salts, beta-hydroxybutyrate esters, and free beta-hydroxybutyric acid(s), to provide a desired electrolyte balance, taste and/or pharmacokinetic response. The compositions can also be combined with short, medium, or long chain fatty acids, esters, glycerides, and other supplements as disclosed herein to provide a desired level of elevated ketone bodies and other effects.

Example 1

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 51% by enantiomeric equivalents of the S-beta-hydroxybutyrate enantiomer and 49% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture. On the other hand, including the S-betahydroxybutyrate enantiomer provides for a longer state of ketosis and/or other benefits as disclosed herein.

The non-racemic mixture is readily administered as a ketogenic composition, such as in powder form as a dietary supplement mixed with food or drink, in the form of one or more capsules or tablets, or in liquid form such as a mouth spray.

Example 2

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 52% by enantiomeric equivalents of the S-beta-hydroxybutyrate enantiomer and 48% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixture of Example 1. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 3

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 53% by enantiomeric equivalents of the S-beta-hydroxybutyrate enantiomer and 47% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1 and 2. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 4

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 55% by enantiomeric equivalents of the S-beta-hydroxybutyrate enantiomer and 45% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-3. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 5

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 57% by enantiomeric equivalents of the S-beta-hydroxybutyrate enantiomer and 43% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-4. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 6

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 60% by enantiomeric equivalents of the S-beta-hydroxybutyrate enantiomer and 40% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-5. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 7

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 65% by enantiomeric equivalents of the S-beta-hydroxybutyrate enantiomer and 35% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-6. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 8

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 70% by enantiomeric equivalents of the S-beta-hydroxybutyrate enantiomer and 30% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-7. On the other hand, including the S-betahydroxybutyrate enantiomer provides for a longer state of ketosis and/or other benefits as disclosed herein, as compared to a composition enriched with the R-beta-hydroxybutyrate enantiomer.

Example 9

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 75% by enantiomeric equivalents of the S-beta-hydroxybutyrate enantiomer and 25% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-8. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 10

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 80% by enantiomeric equivalents of the S-beta-hydroxybutyrate enantiomer and 20% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-9. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 11

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide from 90%, 91%, 92%, 93%, 94%, 95%, 96%, 97%, 98%, 99%, or 99.5% by enantiomeric equivalents of the S-beta-hydroxybutyrate enantiomer and 10%, 9%, 8%, 7%, 6%, 5%, 4%, 3%, 2%, 1%, or 0.5% by enantiomeric equivalents of the R-beta-hydroxybutyrate enantiomer. Because the non-racemic mixture includes substantially less of the R-beta-hydroxybutyrate enantiomer, the onset of ketosis is significantly delayed for a given dosage as compared to the same dosage of racemic mixture or the non-racemic mixtures of Examples 1-10. On the other hand, including the S-beta-hydroxybutyrate enantiomer provides for a longer state of ketosis and/or other benefits as disclosed herein.

Example 12

A composition comprising one or more S-beta-hydroxybutyrate compounds is mixed with a carrier to form a composition with 100% equivalents of S-beta-hydroxybutyrate enantiomer and 0% equivalents of R-beta-hydroxybutyrate enantiomer. Because the composition contains no R-beta-hydroxybutyrate enantiomer, the onset of ketosis is significantly delayed for a given dosage as compared to the same dosage of racemic mixture or the non-racemic mixtures of Examples 1-11. On the other hand, including the S-beta-hydroxybutyrate enantiomer provides for a delayed and/or longer state of ketosis and/or other benefits as disclosed herein.

Example 13

Any of the foregoing examples is modified by combining optically pure S-beta-hydroxybutyrate or non-racemic mixture of S-beta-hydroxybutyrate and R-beta-hydroxybutyrate with a dietetically or pharmaceutically acceptable carrier.

Example 14

Any of the foregoing examples is modified by combining optically pure S-beta-hydroxybutyrate or non-racemic mixture of S-beta-hydroxybutyrate and R-beta-hydroxybutyrate with one or more medium chain triglycerides and/or one or more medium chain fatty acids and/or one or more mono- or diglycerides medium chain fatty acids.

Example 15

Any of the foregoing examples is modified by combining optically pure S-beta-hydroxybutyrate or non-racemic mixture of S-beta-hydroxybutyrate and R-beta-hydroxybutyrate with one or more short chain triglycerides and/or one or more short chain fatty acids and/or one or more mono- or diglycerides of short chain fatty acids Example 16

Any of the foregoing examples is modified by combining optically pure S-beta-hydroxybutyrate or non-racemic mixture of S-beta-hydroxybutyrate and R-beta-hydroxybutyrate with one or more long chain triglycerides and/or one or more long chain fatty acids and/or one or more mono- or diglycerides of long chain fatty acids Example 17

Any of the foregoing examples is modified by combining optically pure S-beta-hydroxybutyrate or non-racemic mixture of S-beta-hydroxybutyrate and R-beta-hydroxybutyrate with one or more supplements, such as vitamin $D_3$, vitamins, minerals, and others known in the art.

Example 18

Any of the foregoing examples is modified by including one or more salts of optically pure S-beta-hydroxybutyrate, or non-racemic mixture of R-beta-hydroxybutyrate and S-beta-hydroxybutyrate, and at least one of S-beta-hydroxybutyric acid or R-beta-hydroxybutyric acid to provide a mixture of S- and/or R-beta-hydroxybutyrate salt(s) and free S- and/or R-beta-hydroxybutyric acid(s), where the mixture contains less than 100% of the one or more beta-hydroxybutyrate salts and greater than 0% of the free beta-hydroxybutyric acid(s), including up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97% by molar equivalents of one or more S-beta-hydroxybutyrate and/or R-beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, by molar equivalents of free S-beta-hydroxybutyric acid and/or free R-beta-hydroxybutyric acid.

Example 19

Any of the foregoing examples is modified by including one or more esters of S-beta-hydroxybutyrate and/or R-beta-hydroxybutyrate and at least one of S-beta-hydroxybutyric acid or R-beta-hydroxybutyric acid to provide a mixture of beta-hydroxybutyrate ester(s) and free S- and/or R-beta-hydroxybutyric acid(s), where the mixture contains less than 100% of the one or more beta-hydroxybutyrate esters and greater than 0% free beta-hydroxybutyric acid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for administering ketone bodies and/or ketone body precursors to a subject, the composition comprising:
    optically pure S-beta-hydroxybutyrate or a non-racemic mixture of S-beta-hydroxybutyrate and R-beta-hydroxybutyrate enriched with S-beta-hydroxybutyrate so as to contain more than 50% and less than 100% by enantiomeric equivalents of S-beta-hydroxybutyrate and less than 50% and more than 0% by enantiomeric equivalents of R-beta-hydroxybutyrate, with the proviso that:
    when the composition comprises the optically pure S-beta-hydroxybutyrate it includes a mixture of at least one optically pure S-beta-hydroxybutyrate salt and optically pure S-beta-hydroxybutyric acid; or
    when the composition comprises the non-racemic mixture of S-beta-hydroxybutyrate and R-beta-hydroxybutyrate it includes a mixture of:
        at least two S-beta-hydroxybutyrate salts;
        at least two R-beta-hydroxybutyrate salts; and
        at least one of S- or R-beta-hydroxybutyric acid.

2. The composition of claim 1, wherein the composition comprises the optically pure S-beta-hydroxybutyrate and includes a plurality of optically pure S-beta-hydroxybutyrate salts and the optically pure S-beta-hydroxybutyric acid and is free of R-beta-hydroxybutyrate salts and R-beta-hydroxybutyric acid.

3. The composition of claim 1, wherein the composition comprises the non-racemic mixture of S-beta-hydroxybutyrate and R-beta-hydroxybutyrate and contains from 50.5% to 99.5% by enantiomeric equivalents of S-beta-hydroxybutyrate and 49.5% to 0.5% by enantiomeric equivalents of R-beta-hydroxybutyrate.

4. The composition of claim 3, wherein the non-racemic mixture of S-beta-hydroxybutyrate and R-beta-hydroxybutyrate contains from 51% to 99% by enantiomeric equivalents of S-beta-hydroxybutyrate and 49% to 1% by enantiomeric equivalents of R-beta-hydroxybutyrate.

5. The composition of claim 3, wherein the non-racemic mixture of S-beta-hydroxybutyrate and R-beta-hydroxybutyrate contains from 52% to 98% by enantiomeric equivalents of S-beta-hydroxybutyrate and 48% to 2% by enantiomeric equivalents of R-beta-hydroxybutyrate.

6. The composition of claim 1, wherein the composition comprises 90% to 99.9% by molar equivalents of at least one optically pure S-beta-hydroxybutyrate salt or 90% to 99.9% by molar equivalents of combined S-beta-hydroxybutyrate and R-beta-hydroxybutyrate salts and 10% to 0.1% by molar equivalents of S-beta-hydroxybutyric acid and/or R-beta-hydroxybutyric acid.

7. The composition of claim 1, wherein the composition comprises 75% to 99.9% by molar equivalents of at least one optically pure S-beta-hydroxybutyrate salt or 75% to 99.9% by molar equivalents of combined S-beta-hydroxybutyrate and R-beta-hydroxybutyrate salts and 25% to 0.1% by molar equivalents of S-beta-hydroxybutyric acid and/or R-beta-hydroxybutyric acid.

8. The composition of claim 1, wherein the non-racemic mixture comprises 85% to 99.8% by molar equivalents of at least one optically pure S-beta-hydroxybutyrate salt or 55% to 99.8% by molar equivalents of combined S-beta-hydroxybutyrate and R-beta-hydroxybutyrate salts and 15% to 0.2% by molar equivalents of S-beta-hydroxybutyric acid and/or R-beta-hydroxybutyric acid.

9. The composition of claim 1, wherein the composition comprises at least one lithium, sodium, potassium, calcium, magnesium, or amino acid salt of S-beta-hydroxybutyrate and/or R-beta-hydroxybutyrate.

10. The composition of claim 1, further comprising at least one short chain fatty acid having less than 6 carbons, or a mono-, di- or triglyceride of the at least one short chain fatty acid.

11. The composition of claim 1, further comprising at least one supplement selected from vitamin, mineral, nootropic, and herbal supplement.

12. A composition for administering ketone bodies and/or ketone body precursors to a subject, the composition comprising:
    optically pure S-beta-hydroxybutyrate or a non-racemic mixture of S-beta-hydroxybutyrate and R-beta-hydroxybutyrate enriched with S-beta-hydroxybutyrate so as to contain more than 50% and less than 100% by enantiomeric equivalents of S-beta-hydroxybutyrate and less than 50% and more than 0% by enantiomeric equivalents of R-beta-hydroxybutyrate, with the proviso that:
    when the composition comprises the optically pure S-beta-hydroxybutyrate it includes a mixture of at least one optically pure S-beta-hydroxybutyrate salt and optically pure S-beta-hydroxybutyric acid; or
    when the composition comprises the non-racemic mixture of S-beta-hydroxybutyrate and R-beta-hydroxybutyrate it includes a mixture of:
        at least one S-beta-hydroxybutyrate salt;
        at least one R-beta-hydroxybutyrate salt; and
        at least one of S- or R-beta-hydroxybutyric acid,
    wherein the composition is provided as or in a tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, or suppository.

13. The composition of claim 12, wherein the composition comprises the non-racemic mixture of S-beta-hydroxybutyrate and R-beta-hydroxybutyrate and contains from 50.5% to 99.5% by enantiomeric equivalents of S-betahydroxybutyrate and 49.5% to 0.5% by enantiomeric equivalents of R-beta-hydroxybutyrate.

14. The composition of claim 12, wherein the composition comprises 75% to 99.9% by molar equivalents of at least one optically pure S-beta-hydroxybutyrate salt or 75% to 99.9% by molar equivalents of combined S-beta-hydroxybutyrate and R-beta-hydroxybutyrate salts and 25% to 0.1% by molar equivalents of S-beta-hydroxybutyric acid and/or R-beta-hydroxybutyric acid.

15. The composition of claim 12, wherein the composition comprises at least one lithium, sodium, potassium, calcium, magnesium, or amino acid salt of S-beta-hydroxybutyrate.

16. The composition of claim 12, further comprising at least one supplement selected from vitamin, mineral, nootropic, and herbal supplement.

17. The composition of claim 12, further comprising:
a dietetically or pharmaceutically acceptable carrier selected from the group consisting of tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, and suppository.

18. A kit for administering ketone bodies to a subject, comprising:
a composition as in claim 1;
a container in which the composition is placed; and
a measuring device configured to hold therein a unit dose, or fraction thereof, of the composition, wherein a unit dose of the composition contains about 0.5 g to about 25 g of the optically pure S-beta-hydroxybutyrate or the non-racemic mixture of S-beta-hydroxybutyrate and R-beta-hydroxybutyrate.

19. The kit of claim 18, wherein the container is selected from the group consisting of carton, box, can, jar, bag, pouch, bottle, jug, and keg.

20. The kit of claim 18, wherein the measuring device is selected from the group consisting of cup, scoop, syringe, dropper, spatula, spoon, and colonic irrigation device.

21. A composition for administering ketone bodies and/or ketone body precursors to a subject, the ketone body composition comprising:
optically pure S-beta-hydroxybutyrate or a non-racemic mixture of S-beta-hydroxybutyrate and R-beta-hydroxybutyrate enriched with S-beta-hydroxybutyrate so as to contain more than 50% and less than 100% by enantiomeric equivalents of S-beta-hydroxybutyrate and less than 50% and more than 0% by enantiomeric equivalents of R-beta-hydroxybutyrate,
wherein the composition comprises one or more salts of S-beta-hydroxybutyrate selected from the group consisting of sodium salt, potassium salt, magnesium salt, transition metal salt, and amino acid salt.

22. A composition for administering ketone bodies and/or ketone body precursors to a subject, the composition comprising:
optically pure S-beta-hydroxybutyrate,
wherein the composition comprises S-beta-hydroxybutyric acid and at least one 5-beta-hydroxybutyrate salt,
wherein the composition is free of R-beta-hydroxybutyrate salts and R-beta-hydroxybutyric acid.

23. A composition for administering ketone bodies and/or ketone body precursors to a subject, the composition comprising:
optically pure S-beta-hydroxybutyrate or a non-racemic mixture of S-beta-hydroxybutyrate and R-beta-hydroxybutyrate enriched with S-beta-hydroxybutyrate so as to contain at least 93% and less than 100% by enantiomeric equivalents of S-beta-hydroxybutyrate and up to 7% and greater than 0% by enantiomeric equivalents of R-beta-hydroxybutyrate, with the proviso that:
when the composition comprises the optically pure S-beta-hydroxybutyrate it includes at least one optically pure S-beta-hydroxybutyrate salt and optically pure S-beta-hydroxybutyric acid; or
when the composition comprises the non-racemic mixture of S-beta-hydroxybutyrate and R-beta-hydroxybutyrate it includes a mixture of:
at least one S-beta-hydroxybutyrate salt;
at least one R-beta-hydroxybutyrate salt; and
at least one of S- or R-beta-hydroxybutyric acid.

24. A composition for administering ketone bodies and/or ketone body precursors to a subject, the composition comprising:
optically pure S-beta-hydroxybutyrate or a non-racemic mixture of S-beta-hydroxybutyrate and R-beta-hydroxybutyrate enriched with S-beta-hydroxybutyrate so as to contain more than 50% and less than 100% by enantiomeric equivalents of S-beta-hydroxybutyrate and less than 50% and more than 0% by enantiomeric equivalents of R-beta-hydroxybutyrate, with the proviso that:
when the composition comprises the optically pure S-beta-hydroxybutyrate it includes 75% to less than 100% by molar equivalents of at least one optically pure S-beta-hydroxybutyrate salt and greater than 0% and up to 25% by molar equivalents of optically pure S-beta-hydroxybutyric acid, or when the composition comprises the non-racemic mixture of S-beta-hydroxybutyrate and R-beta-hydroxybutyrate it includes:
at least one S-beta-hydroxybutyrate salt;
at least one R-beta-hydroxybutyrate salt; and
at least one of S- or R-beta-hydroxybutyric acid,
wherein the non-racemic mixture includes 75% to less than 100% by molar equivalents of combined S-beta-hydroxybutyrate and R-beta-hydroxybutyrate salts, and
wherein the non-racemic mixture includes greater than 0% and up to 25% by molar equivalents of S- and/or R-beta-hydroxybutyric acid.

* * * * *